(12) United States Patent
Fudoji et al.

(10) Patent No.: US 10,987,502 B2
(45) Date of Patent: Apr. 27, 2021

(54) MICRONEEDLE SHEET

(71) Applicant: HISAMITSU PHARMACEUTICAL CO., INC., Tosu (JP)

(72) Inventors: Ryusuke Fudoji, Tokyo (JP); Naoki Yamamoto, Tsukuba (JP)

(73) Assignee: HISAMITSU PHARMACEUTICAL CO., INC., Tosu (JP)

(*) Notice: Subject to any disclaimer, the term of this patent is extended or adjusted under 35 U.S.C. 154(b) by 237 days.

(21) Appl. No.: 16/061,834

(22) PCT Filed: Dec. 6, 2016

(86) PCT No.: PCT/JP2016/086260
§ 371 (c)(1),
(2) Date: Jun. 13, 2018

(87) PCT Pub. No.: WO2017/104491
PCT Pub. Date: Jun. 22, 2017

(65) Prior Publication Data
US 2019/0009070 A1 Jan. 10, 2019

(30) Foreign Application Priority Data

Dec. 15, 2015 (JP) .............................. JP2015-243993

(51) Int. Cl.
*A61M 37/00* (2006.01)
*C08L 67/04* (2006.01)
*C08G 69/10* (2006.01)

(52) U.S. Cl.
CPC ........ *A61M 37/0015* (2013.01); *A61M 37/00* (2013.01); *C08L 67/04* (2013.01);
(Continued)

(58) Field of Classification Search
CPC .............. A61M 37/0015; A61M 37/00; A61M 37/0076; A61M 37/0084;
(Continued)

(56) References Cited

U.S. PATENT DOCUMENTS

2003/0045837 A1* 3/2003 Delmore ........... A61M 37/0015
604/173
2007/0161964 A1* 7/2007 Yuzhakov ......... A61M 37/0015
604/272
(Continued)

FOREIGN PATENT DOCUMENTS

CN 102770176 A 11/2012
CN 104379209 A 2/2015
(Continued)

OTHER PUBLICATIONS

International Search Report dated Mar. 7, 2017 corresponding to application No. PCT/JP2016/086260.
(Continued)

*Primary Examiner* — Lauren P Farrar
(74) *Attorney, Agent, or Firm* — Nath, Goldberg & Meyer; Joshua B. Goldberg

(57) ABSTRACT

The microneedle sheet according to an embodiment comprises a plurality of microneedles formed on a sheet generally along a main surface of the sheet; a bending resistance of the sheet as measured in accordance with a 45° cantilever method defined by JIS L 1096:2010 is 4.2 cm to 12.5 cm; and a material of the sheet is a biodegradable polymer. The microneedles rise from the main surface when the sheet is bent, and the raised microneedles pierce the skin.

2 Claims, 1 Drawing Sheet

(52) U.S. Cl.
CPC ............... *A61M 2037/0023* (2013.01); *A61M 2037/0061* (2013.01); *C08G 69/10* (2013.01)

(58) Field of Classification Search
CPC .. A61M 2037/0061; A61M 2037/0023; A61M 2037/003; A61M 2037/0038; A61M 2037/0053; A61K 9/0021
See application file for complete search history.

(56) References Cited

U.S. PATENT DOCUMENTS

| | | | | |
|---|---|---|---|---|
| 2008/0125743 | A1* | 5/2008 | Yuzhakov | A61M 37/0015 604/506 |
| 2012/0130306 | A1* | 5/2012 | Terahara | A61K 9/0021 604/46 |
| 2013/0041330 | A1* | 2/2013 | Matsudo | A61K 9/0021 604/272 |
| 2013/0150822 | A1* | 6/2013 | Ross | A61K 9/0021 604/501 |
| 2015/0157840 | A1* | 6/2015 | Kominami | A61M 37/0015 600/9 |
| 2015/0352777 | A1* | 12/2015 | DeSimone | A61B 5/150022 106/287.24 |
| 2016/0082240 | A1* | 3/2016 | Ueno | A61K 9/0021 604/46 |
| 2016/0136408 | A1* | 5/2016 | Kato | B29C 39/025 604/173 |
| 2016/0144160 | A1 | 5/2016 | Yamamoto et al. | |
| 2017/0333690 | A1* | 11/2017 | Ogura | A61M 37/0015 |

FOREIGN PATENT DOCUMENTS

| | | | |
|---|---|---|---|
| EP | 2441437 | A1 | 4/2012 |
| EP | 2859910 | A1 | 4/2015 |
| JP | 2003-80619 | A | 3/2003 |
| JP | 2005503210 | A | 2/2005 |
| JP | 2013527853 | A | 7/2013 |
| JP | 2013177376 | A | 9/2013 |
| KR | 1020120138235 | A | 12/2012 |
| KR | 1020150017738 | A | 2/2015 |
| TW | 201410285 | A | 3/2014 |
| WO | 03024518 | A2 | 3/2003 |
| WO | 2008067290 | A2 | 6/2008 |
| WO | 2011105508 | A1 | 9/2011 |
| WO | 2011140274 | A2 | 10/2011 |
| WO | 2013187392 | A1 | 12/2013 |
| WO | WO-2013187392 | A1 * | 12/2013 ............. A61N 2/004 |
| WO | 2014203910 | A1 | 12/2014 |

OTHER PUBLICATIONS

Office Action dated Mar. 19, 2019 issued in corresponding Japanese Application No. 2017-555997.
Office Action dated Dec. 26, 2018 corresponding to Taiwanese application No. 105141182.
Extended European Search Report dated Jul. 5, 2019 corresponding to application No. 16875473.7-1132.
International Preliminary Report on Patentability dated Jun. 28, 2018 corresponding to application No. PCT/JP2016/086260.
Office Action dated Jan. 28, 2020 corresponding to Korean application No. 10-2018-7018841.

* cited by examiner

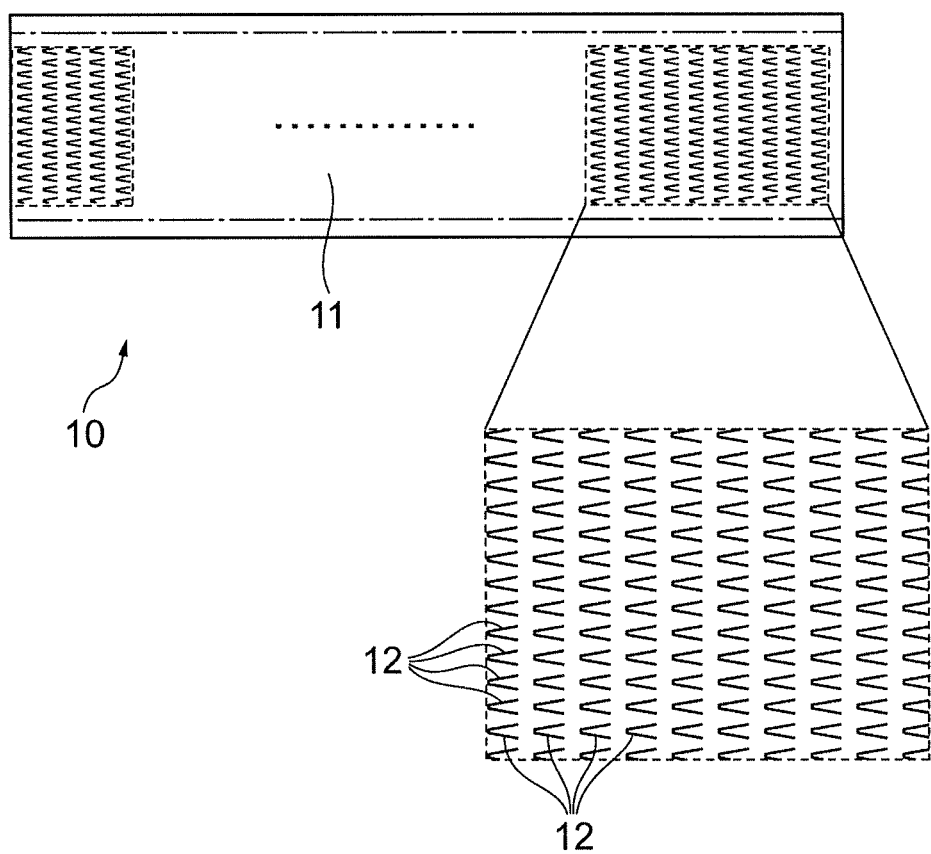

MICRONEEDLE SHEET

This is a National Phase Application filed under 35 U.S.C. 371 as a national stage of PCT/JP2016/086260, filed Dec. 6, 2016, an application claiming the benefit of Japanese Application No. 2015-243993, filed Dec. 15, 2015, the content of each of which is hereby incorporated by reference in its entirety.

TECHNICAL FIELD

One aspect of the present invention relates to a microneedle sheet used to assist in administration of an active ingredient through microneedles.

BACKGROUND ART

Microneedles for administering an active ingredient via the skin and devices including the microneedles have been heretofore known. For example, a rotatable microstructure device described in Patent Literature 1 mentioned below has a curved base material and a roller structure including a plurality of microelements affixed to a first surface of this base material. The plurality of microelements have predetermined size and shape in such a way as to pierce the stratum corneum layer of the skin when the microstructure device is placed on the skin and rolls in the predetermined direction.

CITATION LIST

Patent Literature

Patent literature 1: Japanese Unexamined Patent Publication No. 2005-503210
Patent literature 2: International Publication No. WO 2013/187392

SUMMARY OF INVENTION

Technical Problem

However, in the microstructure device described in the patent literature 1, the microelements are exposed on the roller, and therefore, before trying application of an active ingredient to the skin through microneedles, the needles may come into contact with or may be caught by another object (e.g., a user's skin or clothes). Then, it has been required to ensure safety in handling of the microneedles.

In order to solve such a problem, there has been proposed in Patent Literature 2 a microneedle sheet which includes a plurality of microneedles formed on a sheet generally along a main surface of the sheet and in which the microneedles rise from the main surface when the sheet is bent and the raised microneedles pierce the skin. In such a microneedle sheet, the microneedles are in a state where they are generally along the main surface of the sheet before the sheet is bent. This means that tips of the microneedles do not protrude from the main surface before the microneedles are applied to the skin. Therefore, as long as the microneedle sheet is not applied to the skin, there is no fear that the microneedles come into contact with or are caught by another object. As a result, the safety in handling of the microneedles can be ensured. Here, for such a microneedle sheet, properties that the microneedles easily pierce the skin, that is, puncture properties are required.

Solution to Problem

The microneedle sheet according to one aspect of the present invention comprises a plurality of microneedles formed on a sheet generally along a main surface of the sheet; a bending resistance of the sheet as measured in accordance with a 45° cantilever method defined by JIS L 1096:2010 is 4.2 cm to 12.5 cm; a material of the sheet is a biodegradable polymer; and the microneedles rise from the main surface when the sheet is bent. The raised microneedles pierce the skin.

In such an aspect, the microneedle sheet exhibits excellent puncture properties.

Advantageous Effects of Invention

According to one aspect of the present invention, safety in handling of the microneedles can be ensured, and besides, excellent puncture properties are exhibited.

BRIEF DESCRIPTION OF DRAWINGS

FIG. 1 is a plane view of a microneedle sheet according to an embodiment.

DESCRIPTION OF EMBODIMENTS

In the present specification, the bending resistance means a bending resistance measured in accordance with the 8. 21. 1 A method (45° cantilever method) defined by JIS L 1096:2010. That is to say, the bending resistance means a distance (cm) which a test piece moves, the distance being measured when on a horizontal table with a smooth surface, which has a 45°. slope and is equipped with a scale on its upper surface, the test piece of 5 mm.times.150 mm (microneedle sheet) is arranged in such a way that its short side accords with a base line of the scale, then the test piece is slowly slid in the direction of the slope, and one short side of the test piece comes into contact with the slope.

An embodiment of the present invention will be described in detail hereinafter with reference to the attached drawing.

Using FIG. 1, a structure of a microneedle sheet 10 according the embodiment is described. The microneedle sheet 10 is an instrument to administer an arbitrary active ingredient (e.g., drug) into a living body, and has a large number of microneedles that pierce the skin.

As shown in FIG. 1, the microneedle sheet 10 is in the shape of a band, and has a plurality of microneedles 12 formed on a sheet generally along a main surface 11 of the sheet. These microneedles 12 are lined up in such a way as to be arrayed in each of the longitudinal direction and the width direction of the sheet, and tips of all the microneedles 12 face one end (left direction in FIG. 1) of the sheet without exception.

A bending resistance of the microneedle sheet is 4.2 cm to 12.5 cm. When the bending resistance is in the above range, the microneedle sheet exhibits excellent puncture properties.

A material of the microneedle sheet 10 and the microneedles 12 is a biodegradable polymer. In the present specification, the biodegradable polymer means a polymer compound that is degraded by microorganisms or enzymes in the natural environment or a polymer compound that is degraded or absorbed in vivo. The biodegradable polymer may be a polymer compound derived from organisms or may be a polymer compound semi-synthesized or synthesized. A weight-average molecular weight of the biodegradable polymer is not particularly limited, and may be, for example, about 1 kDa to about 500 kDa.

The biodegradable polymer is not particularly limited as long as it is a biodegradable polymer capable of forming the microneedle sheet 10 and the microneedles 12, and specific examples thereof include ester (co)polymers, polyamino acids and polysaccharides.

Examples of the ester (co)polymers include polymers of aliphatic diols with aliphatic dicarboxylic acids and polymers of hydroxycarboxylic acids, and specific examples thereof include polyglycolic acid (PGA), polyhydroxybutyric acid (PHB), polyhydroxyvaleric acid (PHV), polyhydroxyhexanoic acid, polymalic acid, poly-p-dioxanone (PDO), polycaprolactone (PCL), polylactic acid (poly-L-lactic acid (PLLA), poly-D-lactic acid (PDLA), poly-DL-lactic acid (PDLLA, PDLLA (10:90) (PDLLA in which copolymerization molar ratio between D-lactic acid and L-lactic acid is 10:90))), a lactic acid/glycolic acid copolymer (PLGA, PLGA (50:50) (PLGA in which copolymerization molar ratio between lactic acid and glycolic acid is 50:50), PLGA (75:25) (PLGA in which copolymerization molar ratio between lactic acid and glycolic acid is 75:25)), a glycolic acid/L-lactic acid copolymer (PGLA), a glycolic acid/DL-lactic acid copolymer (PGDLLA), an L-lactic acid/ε-caprolactone copolymer (LCL), a hydroxybutyric acid/hydroxyvaleric acid copolymer (PHB/PHV, P(3HB-co-3HV)), a 3-hydroxybutyric acid/3-hydroxyhexanoic acid copolymer, and a 3-hydroxybutanoic acid/3-hydroxyhexanoic acid copolymer.

Examples of the polyamino acids include polyamino acid, polyaminobutyric acid, peptide, protein, glycoprotein and phosphoprotein, and specific examples thereof include poly-α-amino acids including α-amino acids (one or more kinds selected from the group consisting of alanine, arginine and its salts, asparagine, aspartic acid and its salts, cysteine, glutamine, glutamic acid and its salts, glycine, histidine, isoleucine, leucine, lysine and its salts, hydroxylysine and its salts, methionine, phenylalanine, proline, hydroxyproline, serine, threonine and its salts, tryptophan, tyrosine, valine, and derivatives thereof), polyglutamic acid, polylysine, poly(benzyl glutamate), poly(methyl glutamate), poly-α-aminobutyric acid, poly-β-aminobutyric acid, poly-γ-aminobutyric acid, gelatin, pectin, collagen, albumin, globulin, fibrin, fibrinogen, transferrin, and casein (α-casein, β-casein, κ-casein).

Examples of the polysaccharides include pullulan, hyaluronic acid, chondroitin sulfuric acid, starch, glycogen, pectin, carrageenan, agarose, amylose, amylopectin, xyloglycan, ethylcellulose, methylcellulose, hydroxyethylcellulose, hydroxypropylcellulose, hydroxyproylmethylcellulose, dextran, dextrin, carmellose, chitosan, alginic acid, and salts thereof.

As the biodegradable polymers, polylactic acid, a lactic acid/glycolic acid copolymer, and polyglutamic acid are preferable from the viewpoint of puncture properties of the microneedle sheet. Moreover, as the biodegradable polymers, pullulan, hyaluronic acid, chondroitin sulfuric acid, carmellose, and salts thereof are preferable from the viewpoint of puncture properties of the microneedle sheet.

The microneedle sheet 10 and the microneedles 12 may further contain water, acids, bases, salts, saccharides, polysaccharides, alcohols, polyhydric alcohols, oils and fats, biologically active substances, etc., in addition to the biodegradable polymer.

Examples of the acids include inorganic acids, such as hydrochloric acid, hydrobromic acid, nitric acid, sulfuric acid and phosphoric acid, and organic acids, such as maleic acid, maleic anhydride, phosphoric acid, benzenesulfonic acid, methanesulfonic acid, citric acid, succinic acid, glycolic acid, gluconic acid, glucuronic acid, lactic acid, malic acid, pyruvic acid, tartaric acid, tartronic acid, fumaric acid, acetic acid, propionic acid, butanoic acid, pentanoic acid, carbonic acid, malonic acid, adipic acid, citraconic acid, levulinic acid, glutaric acid, itaconic acid, meglutol, mesaconic acid, citramalic acid, aspartic acid, glutamic acid, tricarballylic acid and ethylenediaminetetraacetic acid.

Examples of the bases include inorganic bases, such as sodium hydroxide and potassium hydroxide, and organic bases, such as monoethanolamine, triethanolamine and diethanolamine.

Examples of the salts include sodium chloride, magnesium chloride, sodium acetate, sodium carbonate, sodium hydrogenphosphate (disodium hydrogenphosphate, sodium dihydrogenphosphate), potassium hydrogenphosphate (dipotassium hydrogenphosphate, potassium dihydrogenphosphate), sodium lactate, potassium sulfate and magnesium sulfate.

Examples of the saccharides include trehalose, sucrose, lactose, fructose, galactose, mannose, maltose, glucose, mannitol and sorbitol.

Examples of the polysaccharides include pullulan, hyaluronic acid, chondroitin sulfuric acid, starch, glycogen, pectin, carrageenan, agarose, amylose, amylopectin, xyloglycan, ethylcellulose, methylcellulose, hydroxyethylcellulose, hydroxypropylcellulose, hydroxypropylmethylcellulose, dextran, dextrin, carmellose, chitosan, alginic acid, and salts thereof.

Examples of the alcohols include isopropanol, propanol, butanol, lauryl alcohol, myristyl alcohol, oleyl alcohol, isostearyl alcohol and octyldodecanol.

Examples of the polyhydric alcohols include glycerol, ethylene glycol, propylene glycol, dipropylene glycol and 1,3-butylene glycol.

Examples of the oils and fats include sesame oil, olive oil, soybean oil, *camellia* oil, castor oil and peanut oil.

The biologically active substance is not particularly limited as long as it is a substance exerting some action on a living body, and examples thereof include low-molecular compounds, peptide, protein, and derivatives thereof.

Examples of the low-molecular compounds include hypnotic/sedative drugs (flurazepam hydrochloride, rilmazafone hydrochloride, phenobarbital, amobarbital, etc.), antipyretic anti-inflammatory analgesic drugs (butorphanol tartrate, perisoxal citrate, acetaminophen, mefenamic acid, diclofenac sodium, aspirin, alclofenac, ketoprofen, flurbiprofen, naproxen, piroxicam, pentazocine, indomethacin, glycol salicylate, aminopyrine, loxoprofen, etc.), steroid-based anti-inflammatory drugs (hydrocortisone, prednisolone, dexamethasone, betamethasone, etc.), stimulant/antihypnotic agents (methamphetamine hydrochloride, methylphenidate hydrochloride, etc.), psychotropic agents (imipramine hydrochloride, diazepam, sertraline hydrochloride, fluvoxamine maleate, paroxetine hydrochloride, citalopram hydrobromide, fluoxetine hydrochloride, alprazolam, haloperidol, clomipramine, amitriptyline, desipramine, amoxapine, maprotiline, mianserin, setiptiline, trazadone, lofepramine, milnacipran, duloxetine, venlafaxine, chlorpromazine hydrochloride, thioridazine, diazepam, meprobamate, etizolam, etc.), hormone drugs (estradiol, estriol, progesterone, norethisterone acetate, metenolone acetate, testosterone, etc.), local anesthetics (lidocaine hydrochloride, procaine hydrochloride, tetracaine hydrochloride, dibucaine hydrochloride, propitocaine hydrochloride, etc.), agents affecting urinary organs (oxybutynin hydrochloride, tamsulosin hydrochloride, propiverine hydrochloride, etc.), skeletal muscle relaxants (tizanidine hydrochloride, eperisone hydrochloride, pridinol mesylate, suxamethonium hydrochloride, etc.), agents affecting genital organs (ritodrine hydrochloride, meluadrine tartrate), antiepileptic agents (sodium valproate, clonazepam, carbamazepine, etc.), autonomic agents (carpronium chloride, neostigmine bromide, bethanechol chloride, etc.), antiparkinsonian agents (pergolide mesylate, bromocriptine mesylate, trihexyphenidyl hydrochloride, amantadine hydrochloride, ropinirole hydrochloride, talipexole hydrochloride, cabergoline, droxidopa, biperiden, selegiline hydrochloride, etc.), diuretics (hydroflumethiazide, furosemide, etc.), respiratory stimulants (lobeline hydrochloride, dimorpholamine, naloxone hydrochloride, etc.), antimigraine drugs (dihydroergotamine mesylate, sumatriptan, ergotamine tartrate, flunarizine hydrochloride, cyproheptadine hydrochloride, etc.), antihistamines (clemastine fumarate, diphenhydramine tannate, chlorpheniramine maleate, diphenylpyraline hydrochloride, promethazine, etc.), bronchodilators (tulobuterol hydrochloride, procaterol hydrochloride, salbutamol sulfate, clenbuterol hydrochloride, fenoterol hydrobromide, terbutaline sulfate, isoprenaline sulfate, formoterol fumarate, etc.), cardiotonic drugs (isoprenaline hydrochloride, dopamine hydrochloride, etc.), coronary vasodilators (diltiazem hydrochloride, verapamil hydrochloride, isosorbide nitrate, nitroglycerin, nicorandil, etc.), peripheral vasodilators (nicametate citrate, tolazoline hydrochloride, etc.), smoking cessation aids (nicotine, etc.), cardiovascular agents (flunarizine hydrochloride, nicardipine hydrochloride, nitrendipine, nisoldipine, felodipine, amlodipine besylate, nifedipine, nilvadipine, manidipine hydrochloride, benidipine hydrochloride, enalapril maleate, temocapril hydrochloride, alacepril, imidapril hydrochloride, cilazapril, lisinopril, captopril, trandolapril, perindopril erbumine, atenolol, bisoprolol fumarate, metoprolol tartrate, betaxolol hydrochloride, arotinolol hydrochloride, celiprolol hydrochloride, carvedilol, carteolol hydrochloride, bevantolol hydrochloride, valsartan, candesartan cilexetil, losartan potassium, clonidine hydrochloride, etc.), antiarrhythmic agents (propranolol hydrochloride, alprenolol hydrochloride, procainamide hydrochloride, mexiletine hydrochloride, nadolol, disopyramide, etc.), antineoplastic drugs (cyclophosphamide, fluorouracil, tegafur, procarbazine hydrochloride, ranimustine, irinotecan hydrochloride, fluridine, etc.), antilipemic agents (pravastatin, simvastatin, bezafibrate, probucol, etc.), hypoglycemic agents (glibenclamide, chlorpropamide, tolbutamide, glymidine sodium, glybuzole, buformin hydrochloride), peptic ulcer agents (proglumide, cetraxate hydrochloride, spizofurone, cimetidine, glycopyrronium bromide), cholagogues (ursodeoxycholic acid, osalmid, etc.), gastrointestinal prokinetic agents (domperidone, cisapride, etc.), agents for liver disease (tiopronin, etc.), antialergic agents (ketotifen fumarate, azelastine hydrochloride, etc.), antiviral drugs (acyclovir, etc.), antimotionsickness agents (betahistine mesylate, diphenidol hydrochloride, etc.), antibiotic drugs (cefaloridine, cefdinir, cefpodoxime proxetil, cefaclor, clarithromycin, erythromycin, methyl erythromycin, kanamycin sulfate, cycloserine, tetracycline, benzylpenicillin potassium, propicillin potassium, cloxacillin sodium, ampicillin sodium, bacampicillin hydrochloride, carbenicillin sodium, chloramphenicol, etc.), agents for habitual intoxication (cyanamide, etc.), appetite suppressants (mazindol, etc.), chemotherapeutic agents (isocyanide, ethionamide, pyrazinamide, etc.), blood coagulation accelerators (ticlopidine hydrochloride, warfarin potassium), anti-Alzheimer's agents (physostigmine, donepezil hydrochloride, tacrine, arecoline, xanomeline, etc.), serotonin receptor antagonist antiemetics (ondansetron hydrochloride, granisetron hydrochloride, ramosetron hydrochloride, azasetron hydrochloride, etc.), gout treatment agents (colchicine, probenecid, sulfinpyrazone, etc.), and narcotic analgesic drugs (fentanyl citrate, morphine sulfate, morphine hydrochloride, codeine phosphate, cocaine hydrochloride, pethidine hydrochloride, etc.).

Examples of the peptides and proteins include α-interferon, β-interferon for multiple sclerosis, erythropoietin, follitropin β, follitropin α, G-CSF, GM-CSF, human chorionic gonadotropin, luteinizing (leutinizing) hormone, salmon calcitonin, glucagon, GNRH antagonist, insulin, human growth hormone, filgrastim, heparin, low-molecular weight heparin, somatropin, incretin, and GLP-1 derivatives. Examples of the vaccines include Japanese encephalitis vaccine, rotavirus vaccine, Alzheimer's disease vaccine, arteriosclerosis vaccine, cancer vaccine, nicotine vaccine, diphtheria vaccine, tetanus vaccine, pertussis vaccine, Lyme disease vaccine, rabies vaccine, pneumococcal vaccine, yellow fever vaccine, cholera vaccine, vaccinal eruption vaccine, tuberculosis vaccine, rubella vaccine, measles vaccine, mumps vaccine, botulinum vaccine, herpes virus vaccine, other DNA vaccines, and hepatitis B vaccine.

The microneedles 12 can be formed by laser or the like. By evaporating a sheet by laser, the microneedles 12 can be formed. In the present embodiment, the microneedles 12 are each in the shape of a triangle, as shown in FIG. 1, but the shape of the microneedle is in no way limited. Since there is no need to raise the microneedles 12 from the main surface 11 in advance, the microneedle sheet 10 can be produced easily and inexpensively.

Also a thickness of the microneedle sheet 10 is not limited. Specifically, the lower limit of the thickness of the microneedle sheet 10 may be 5 μm, 20 μm or 40 μm, and the upper limit of the thickness may be 1000 μm, 300 μm, 110 μm or 80 μm. The lower limit of the thickness of the microneedle sheet 10 is determined taking into consideration strength of the microneedles 12 that pierce the skin, and the upper limit of the thickness is determined taking into consideration bendability of the sheet, puncture properties of the microneedles 12, etc.

In the microneedle sheet according to one aspect of the present invention, the thickness of the sheet may be 20 μm to 110 μm, may be 40 μm to 110 μm, may be 20 μm to 80 μm, or may be 40 μm to 80 μm. By setting the thickness as above, the puncture properties of the microneedle sheet become excellent. Moreover, by setting the thickness as above, the microneedle sheet becomes thin and flexible, so that the sheet can be applied to the skin in accordance with the shape of a living body, and as a result, an active ingredient can be efficiently administered.

Also a length and a width of the microneedle sheet 10 are not limited. Specifically, the lower limit of the length of the microneedle sheet 10 may be 0.1 cm or 1 cm, and the upper limit of the length may be 50 cm or 20 cm. The lower limit of the width of the microneedle sheet 10 may be 0.1 cm or 1 cm, and the upper limit of the width may be 60 cm or 30 cm. The lower limits of the length and the width of the microneedle sheet 10 are determined taking dose of an active ingredient into consideration, and the upper limits of the length and the width are determined taking a size of a living body into consideration.

Also parameters regarding the microneedles 12 are not limited. Specifically, the lower limit of a length of the microneedle 12 may be 10 μm or 100 μm, and the upper limit of the length thereof may be 10000 μm or 1000 μm. Here, the length of the microneedle 12 is a distance from the base (portion of a root that rises from the main surface 11) of the microneedle 12 to the top thereof. The lower limit of a density of the needles may be 0.05 needles/cm$^2$ or 1 needle/cm$^2$, and the upper limit of the density may be 10000 needles/cm$^2$ or 5000 needles/cm$^2$. The lower limit of the density is a value converted from the number of needles capable of administering 1 mg of an active ingredient and from the area, and the upper limit of the density is a threshold value upon consideration of the shape of the needles.

In the present embodiment, the microneedle 12 is in the shape of a triangle, as shown in FIG. 1, but the shape of the microneedle is in no way limited. Moreover, in the present embodiment, the sizes and the directions of the microneedles 12 and the distribution thereof in the microneedle sheet are uniform, as shown in FIG. 1, but none of them need to be uniform. When the microneedle 12 is in the shape of a triangle, the angle of its tip may be 10° or more, may be 20° or more, may be 150° or less, or may be 120° or less.

As methods for preparing an active ingredient applied to the skin, a technique of allowing the microneedle sheet 10 itself to contain an active ingredient inside (in this case, the active ingredient may be in either a state of being dissolved or a state of being dispersed in the microneedle sheet), a technique of coating the microneedle sheet 10 itself with an active ingredient in advance, a technique of adding a layer containing an active ingredient as an upper layer on the microneedle sheet 10 containing or not containing the active ingredient, a technique of applying an active ingredient to the skin before puncture of the skin with the microneedles 12, and a technique of applying an active ingredient to the skin after puncture of the skin with the microneedles 12 can be thought. When the microneedle sheet 10 is coated with an active ingredient in advance, it is preferable to apply a coating solution of a prescribed viscosity all over the sheet in a thickness that is as uniform as possible, and such application can be easily carried out because the microneedles 12 are along the main surface 11. The coating may be carried out using the principle of screen printing, or may be carried out by other methods.

When the microneedle sheet 10 is applied to the skin, an applicator can be used. Known applicators, such as an applicator described in International Publication No. WO 2014/203911, are available.

As described above, the microneedle sheet according to one aspect of the present invention comprises a plurality of microneedles formed on a sheet generally along a main surface of the sheet, and the microneedles rise from the main surface when the sheet is bent, and the raised microneedles pierce the skin.

In such an aspect, the microneedles are in a state where they are generally along the main surface of the sheet before the sheet is bent. This means that tips of the microneedles do not protrude from the main surface before the microneedles are applied to the skin. Therefore, as long as the microneedle sheet is not applied to the skin, there is no fear that the microneedles come into contact with or are caught by another object. As a result, the safety in handling of the microneedles can be ensured. For example, a user can safely carry out storage and transportation of the microneedle sheet and preparation thereof immediately before use.

EXAMPLES

The present invention will be specifically described below with reference to examples, but the present invention is in no way limited to the examples.

Test Example 1: Measurement of Bending Resistance and Evaluation of Puncture Properties (Preparation of Microneedle Sheet)

After each material was dissolved in water or acetonitrile, the material was cast onto a plastic film and air-dried to obtain each polymer film. The prepared each polymer film was subjected to laser processing to prepare each microneedle sheet.

As the material, PLGA (50:50), PLGA (75:25), PDLLA (weight-average molecular weight: 140000), PDLLA (10:90) or polyglutamic acid was used. Moreover, as the material, pullulan, chondroitin sodium sulfate, sodium hyaluronate or carmellose sodium was used.

(Bending Resistance Test)

A bending resistance was measured in accordance with the 8. 21. 1 A method defined by JIS L 1096:2010. Specifically, on a horizontal table with a smooth surface, which had a 45°. slope and was equipped with a scale on its upper surface, a test piece obtained by cutting the microneedle sheet prepared above into 5 mm×150 mm was arranged in such a way that its short side accorded with a base line of the scale, then the test piece was slowly slid in the direction of the slope, and a distance (cm) which the test piece had moved by the time a central point of one short side of the test piece came into contact with the slope was measured.

(Evaluation Method for Puncture Properties)

One end of the microneedle sheet prepared above and one end of a film having almost the same size as the microneedle sheet and a thickness of 75 μm were fixed to each other. Between a styrene copolymer elastomer sheet as a model of the skin and a flexible flat plate having an interval of about 100 μm from the elastomer sheet, the microneedle sheet to which the film had been fixed was arranged, and its one end was fixed to the styrene copolymer elastomer sheet. While the film was pulled in the horizontal direction to subject the microneedle sheet to 180° bending, the styrene copolymer elastomer sheet was punctured with the microneedles. The hardness of the styrene copolymer elastomer sheet is 30 in terms of International Rubber Hardness Degrees as defined by JIS K 6253-2:2012.

Evaluation of puncture properties was carried out by evaluating each item of 1) 180° bendability of microneedle sheet, 2) rising properties of microneedles, 3) mobility of bending portion of microneedle sheet, and 4) bending properties of microneedles, and then making comprehensive evaluation of these items. Specifically, evaluation was made based on the following criteria.

1) 180° Bendability of Microneedle Sheet

A case where the microneedle sheet broke just by bending the sheet was evaluated as X, and a case where the microneedle sheet did not break even by bending the sheet was evaluated as ◯.

2) Rising Properties of Microneedles

A case where the microneedles did not rise was evaluated as X, and a case where the microneedles rose was evaluated as ◯.

3) Mobility of Bending Portion of Microneedle Sheet

A case where the microneedle sheet broke when feeding of the sheet was tried was evaluated as X, and a case where the microneedle sheet did not break even though the sheet was fed was evaluated as ○.

4) Bending Properties of Microneedles

A case where the microneedles themselves bent and did not easily pierce the styrene copolymer elastomer sheet was evaluated as X, and a case where the microneedles did not bend but pierced the styrene copolymer elastomer sheet was evaluated as ○.

5) Puncture Properties

A case where there was not even one X in the above evaluations 1) to 4) was evaluated as ○, and other cases were evaluated as X.

The results are shown in Table 1 and Table 2.

TABLE 1

| Material | Thickness (μm) | Bending resistance (cm) | 180° Bendability of microneedle sheet | Rising properties of microneedles | Mobility of bending portion of microneedle sheet | Bending properties of microneedles | Puncture properties |
| --- | --- | --- | --- | --- | --- | --- | --- |
| PLGA (50:50) | 110 | 10.1 | ○ | ○ | ○ | ○ | ○ |
| PLGA (50:50) | 80 | 8.9 | ○ | ○ | ○ | ○ | ○ |
| PLGA (50:50) | 40 | 5.7 | ○ | ○ | ○ | ○ | ○ |
| PLGA (50:50) | 30 | 4.2 | ○ | ○ | ○ | ○ | ○ |
| PLGA (50:50) | 25 | 3.8 | ○ | ○ | ○ | X | X |
| PLGA (75:25) | 100 | 10.3 | ○ | ○ | ○ | ○ | ○ |
| PLGA (75:25) | 80 | 8.4 | ○ | ○ | ○ | ○ | ○ |
| PLGA (75:25) | 50 | 5.3 | ○ | ○ | ○ | ○ | ○ |
| PLGA (75:25) | 40 | 4.8 | ○ | ○ | ○ | ○ | ○ |
| PLGA (75:25) | 30 | 3.9 | ○ | ○ | ○ | X | X |
| PDLLA (Mw: 140000) | 110 | 10.2 | ○ | ○ | ○ | ○ | ○ |
| PDLLA (Mw: 140000) | 80 | 8.9 | ○ | ○ | ○ | ○ | ○ |
| PDLLA (Mw: 140000) | 50 | 5.5 | ○ | ○ | ○ | ○ | ○ |
| PDLLA (Mw: 140000) | 30 | 4.1 | ○ | ○ | ○ | X | X |
| PDLLA (10:90) | 80 | 9.3 | ○ | ○ | ○ | ○ | ○ |
| PDLLA ((10:90) | 30 | 4.0 | ○ | ○ | ○ | X | X |
| Polyglutamic acid | 110 | 14.1 | ○ | ○ | X | ○ | X |
| Polyglutamic acid | 90 | 12.5 | ○ | ○ | ○ | ○ | ○ |
| Polyglutamic acid | 70 | 9.9 | ○ | ○ | ○ | ○ | ○ |
| Polyglutamic acid | 60 | 9.3 | ○ | ○ | ○ | ○ | ○ |
| Polyglutamic acid | 45 | 8.0 | ○ | ○ | ○ | ○ | ○ |
| Polyglutamic acid | 20 | 4.2 | ○ | ○ | ○ | ○ | ○ |
| Polyglutamic acid | 10 | 3.3 | ○ | ○ | ○ | X | X |

TABLE 2

| Material | Thickness (μm) | Bending resistance (cm) | 180° Bendability of microneedle sheet | Rising properties of microneedles | Mobility of bending portion of microneedle sheet | Bending properties of microneedles | Puncture properties |
| --- | --- | --- | --- | --- | --- | --- | --- |
| Pullulan | 110 | 13.75 | ○ | ○ | X | ○ | X |
| | 100 | 11.85 | ○ | ○ | ○ | ○ | ○ |
| | 50 | 8 | ○ | ○ | ○ | ○ | ○ |
| | 30 | 5.75 | ○ | ○ | ○ | ○ | ○ |
| | 23 | 4.8 | ○ | ○ | ○ | ○ | ○ |
| | 18 | 3.9 | ○ | ○ | ○ | X | X |
| Chondroitin sodium sulfate | 110 | 12.65 | ○ | ○ | X | ○ | X |
| | 100 | 10.65 | ○ | ○ | ○ | ○ | ○ |
| | 50 | 7.8 | ○ | ○ | ○ | ○ | ○ |
| | 30 | 5.35 | ○ | ○ | ○ | ○ | ○ |
| | 23 | 4.85 | ○ | ○ | ○ | ○ | ○ |
| | 20 | 4.4 | ○ | ○ | ○ | ○ | ○ |
| Sodium hyaluronate | 70 | 9.2 | ○ | ○ | ○ | ○ | ○ |
| | 50 | 8.60 | ○ | ○ | ○ | ○ | ○ |
| | 30 | 6.25 | ○ | ○ | ○ | ○ | ○ |
| | 22 | 4.95 | ○ | ○ | ○ | ○ | ○ |
| | 20 | 4.45 | ○ | ○ | ○ | ○ | ○ |
| Carmellose sodium | 80 | 9.95 | ○ | ○ | ○ | ○ | ○ |
| | 60 | 8.85 | ○ | ○ | ○ | ○ | ○ |
| | 40 | 6.25 | ○ | ○ | ○ | ○ | ○ |
| | 30 | 5.4 | ○ | ○ | ○ | ○ | ○ |
| | 25 | 5.15 | ○ | ○ | ○ | ○ | ○ |
| | 20 | 4.3 | ○ | ○ | ○ | ○ | ○ |

In the test pieces whose bending resistance was in the range of 4.2 cm to 12.5 cm, the mobility of bending portion of microneedle sheet and the bending properties of microneedles were both good, and the test pieces exhibited excellent puncture properties.

REFERENCE SIGNS LIST

10: Microneedle sheet, 11: Main surface, 12: Microneedle

The invention claimed is:

1. A microneedle sheet comprising a plurality of microneedles formed on a sheet generally along a main surface of the sheet, wherein
    a bending resistance of the sheet as measured in accordance with a 45° cantilever method defined by JIS L 1096:2010 is 4.2 cm to 12.5 cm, thereby providing improved puncture properties to the microneedle sheet such that the plurality of microneedles do not bend but pierce a styrene copolymer elastomer test sheet,
    a material of the sheet is selected from the group consisting of polylactic acid, a lactic acid/glycolic acid copolymer, polyglutamic acid, pullulan or a salt thereof, hyaluronic acid or a salt thereof, chondroitin sulfuric acid or a salt thereof, and carmellose or a salt thereof,
    a thickness of the sheet is 40 μm to 80 μm, and
    the microneedles rise from the main surface when the sheet is bent.

2. The microneedle sheet according to claim 1, wherein the material of the sheet is polyglutamic acid.

* * * * *